May 7, 1940. J. F. STYER Plant Pat. 390
CHRYSANTHEMUM PLANT
Filed June 20, 1939
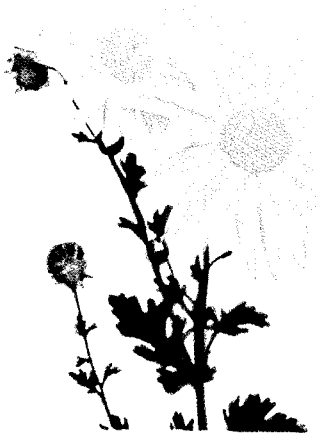
Fig. I
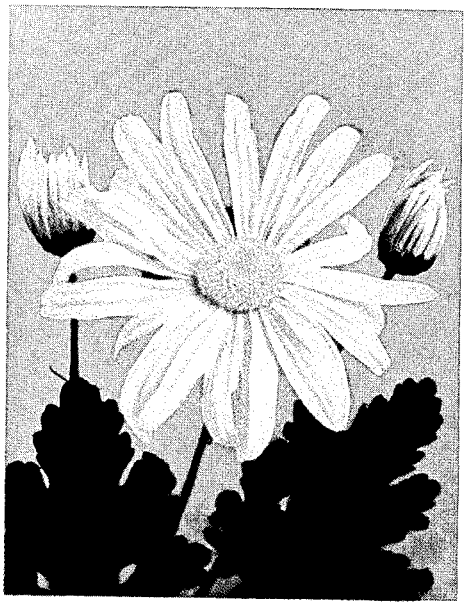
Fig. II
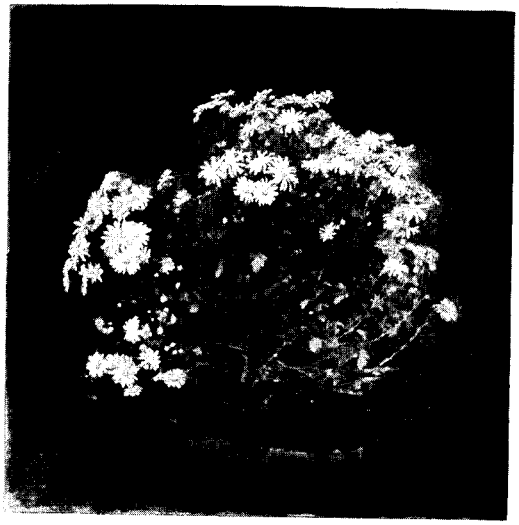
Fig. III
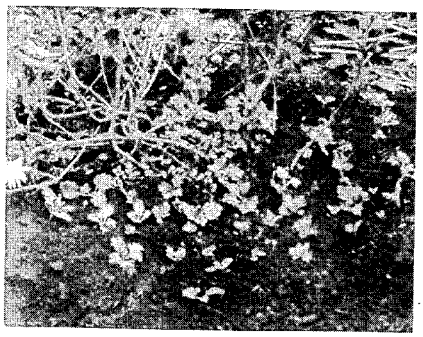
Fig IV
INVENTOR
John Franklin Styer
By Orville M. Kile
Plant Patent Agent Patented May 7, 1940

UNITED STATES PATENT OFFICE

390

CHRYSANTHEMUM PLANT

John Franklin Styer, Concordville, Pa.

Application June 20, 1939, Serial No. 280,172

1 Claim. (Cl. 47—60)

My invention relates to improvements in hardy perennial chrysanthemums and consists of a new and improved variety, differing radially in plant form and growth features from previously known chrysanthemums, with the single exception of the variety Astrid which is the parent of the present variety, from which it differs in several important respects, particularly in color. The present variety has a color range from Lemon Yellow to Cadmium Orange while the parent variety has flowers with petals of a color approximately Rose Pink with a suffusion of Apricot Buff. The color of the new variety fades much less than that of its parent.

This new variety was obtained by the inventor from seed produced by self-fertilization of the variety Astrid, which is believed to be a hybrid of *Chrysanthemum articum* with an unknown garden chysanthemum, and which originated on my property in Concordville. I planted the seeds of Astrid from which a large number of seedlings were produced. In the mass these seedlings exhibited certain variations in such numbers as to indicate them to be the second generation of a true hybrid. This new variety was selected from these seedlings, has been reproduced asexually, and retains its distinguishing characteristics.

The fundamental improvement which distinguishes this new class of chrysanthemums is found in the plant and crown growth. The crown produces numerous underground stems which assure the winter-hardiness of the variety and which are capable of producing new plants which will, under conditions to be described, bloom normally in the spring. The plants of this new variety may be lifted in mid-winter and divided, and plants so made may be grown indoors producing normal flowers of dependable quantity and quality about the month of May, on stems approximately 16 inches in height. This feature is inherent in the race of hybrid chrysanthemums of which this variety is a member and especially serves to set this variety apart from chrysanthemums of previously known types, in which the feature was at best sporadic and abnormal.

The plant of this variety is exceptionally vigorous and grows into perfect compact globe-shape without shearing or pinching. It is extremely hardy as a result of the vigorous and early crown growth, and is perfectly winter-hardy at Concordville, Pennsylvania.

The accompanying illustrations show different phases of this plant as follows: Fig. I, typical fall flowers; Fig. II, typical spring flowers; Fig. III, the plant as it appears in the fall; and Fig. IV, the crown growth as it appears in the fall.

In the following detailed description of this new variety of chrysanthemum, color plate references indicate Ridgway's Color Standards and Nomenclature. When no plate numbers are given the ordinary dictionary definition is intended.

*The plant*

Growth: The plant is approximately globe-shaped. The stems branch naturally at or within 6 inches above ground, these branches usually branching again between 10 and 18 inches above ground, the outer branches turning upward. Thus approximately 25 to 35 branches are produced which elongate and bear sprays of flowers in a high open arrangement.

*Size.*—Average height of a one-year plant is 23 inches; width 36 inches.

*Sprays.*—Usually bear three to six flowers.

*Crown.*—During the growing season the crown is extended by underground stems mostly 5 to 12 inches in length, which turn upward and bear leafy tips ¼ to 2 inches above the surface. The crown thus becomes 16 to 28 inches wide.

Foliage:

*Leaf blade.*—Usually 1½ to 2¾ inches wide and 2 to 3 inches long. Has five main lobes between which the leaf is cut ⅜ to 1 inch deep, the margin of each lobe sharply toothed in the same proportion.

*Petiole.*—One-half to ⅞ inch long.

*Color.*—Upper side Elm Green (Plate XVII). Under side Biscay Green (Plate XVII).

*Substance.*—Medium weight.

Stems:

*Color.*—Biscay Green (Plate XVII), sometimes touched with reddish tinge.

*Size.*—Medium.

Blooming: Fall season starts between October 12 and 16 in my gardens in Concordville, Pennsylvania.

*The flower*

Blossom:

*Size.*—Usually 3 to 4½ inches across.

*Form.*—Single row of 20 to 30 ray flowers surrounding a raised center or cushion about ¾ to ⅞ inch across.

*Ray flowers.*—Size—one and three-eighths to 1⅝ inches long by ¼ to ⅜ inch wide. Color—in the fall the color ranges from Amber Yellow (Plate XVI) to Lemon Chrome (Plate IV). In the spring the colors are slightly deeper in tone, ranging from Lemon Yellow (Plate IV) through Chrome (Plate IV), to include some Apricot Yellow (Plate IV) in the younger flowers. The colors of both the spring and fall flowers have a much greater brilliance and gloss than is shown in the color plates. The reverse of the petals is dull and slightly lighter than the upper surface. Showing through between the yellow ray flowers of the opening bud are stripes of Raw Sienna to Cadmium Orange (Plate III). Shape—slightly wider in middle; ends rounded-blunt. Texture—smooth, with few parallel ridges. Substance—of medium weight.

*Cushion.*—The cushion or raised center is in standard concentric pattern of Compositae, and is composed of many pollen-bearing florets. It is cone-shaped, the center being ¾ inch high.

*Florets.*—The center florets are ¼ inch in length, with a pistil which extends ⅛ inch beyond the end of the corolla. Color—Wax Yellow (Plate XVI).

Having thus disclosed my invention, I claim:

A new and distinct variety of perennial chrysanthemum substantially as shown and described, characterized particularly by its vigor and hardiness; its compact globe shape, its blossoms of Amber Yellow to Apricot Yellow, with high large yellow cushion-center; and its unusual crown growth which enables it to normally produce flowers in the spring as well as in the fall.

JOHN FRANKLIN STYER.